United States Patent
Jannasch

(10) Patent No.: US 7,388,203 B2
(45) Date of Patent: Jun. 17, 2008

(54) NON-CONTACT EXHAUST GAS MEASUREMENT BY MEANS OF FTIR SPECTROMETRY IN METALLURGICAL INSTALLATIONS

(75) Inventor: Otmar Jannasch, Moers (DE)

(73) Assignee: SMS Demag AG, Dusseldorf (DE)

( * ) Notice: Subject to any disclaimer, the term of this patent is extended or adjusted under 35 U.S.C. 154(b) by 0 days.

(21) Appl. No.: 11/659,933

(22) PCT Filed: Jun. 24, 2005

(86) PCT No.: PCT/EP2005/006848

§ 371 (c)(1),
(2), (4) Date: Feb. 8, 2007

(87) PCT Pub. No.: WO2006/015660

PCT Pub. Date: Feb. 16, 2006

(65) Prior Publication Data

US 2007/0296976 A1    Dec. 27, 2007

(30) Foreign Application Priority Data

Aug. 12, 2004  (DE) .................... 10 2004 039 076

(51) Int. Cl.
*G01J 5/02* (2006.01)
(52) U.S. Cl. ................................. 250/339.08
(58) Field of Classification Search ............. 250/339.08
See application file for complete search history.

(56) References Cited

U.S. PATENT DOCUMENTS

| 3,720,404 | A |  | 3/1973 | Carleton et al. |
| 3,871,871 | A |  | 3/1975 | Denis et al. |
| 4,911,914 | A | * | 3/1990 | Satake et al. ............. 423/594.1 |
| 4,928,015 | A | * | 5/1990 | Butler et al. ................ 250/343 |
| 5,984,998 | A |  | 11/1999 | Ottesen et al. |
| 7,022,992 | B2 | * | 4/2006 | Grant et al. ............ 250/339.13 |
| 2003/0160174 | A1 | * | 8/2003 | Grant et al. ............ 250/339.13 |

* cited by examiner

*Primary Examiner*—David P. Porta
*Assistant Examiner*—Mark R Gaworecki
(74) *Attorney, Agent, or Firm*—Abelman, Frayne & Schwab

(57) ABSTRACT

During carrying out metallurgical processes in plant components such as, e.g., a converter, knowledge of a time-dependent exhaust gas composition provides a significant aid in obtaining information about the process advancement. Known analytical methods consist in taking of a limited volume from the exhaust gas flow (7) and then analyzing this exhaust gas sample. The drawback of an analytical method, which is based on sampling, consists in the time delay with which the results of the analysis can be first obtained after sampling. The invention proposes to carry out a non-contact exhaust gas analysis without a time delay using FTIR-spectrometry, whereby obtained spectra of a FTIR-spectrometer (2) are used for calculating the exhaust gas composition, using a preliminary established mathematical model (Drawing figure).

8 Claims, 1 Drawing Sheet

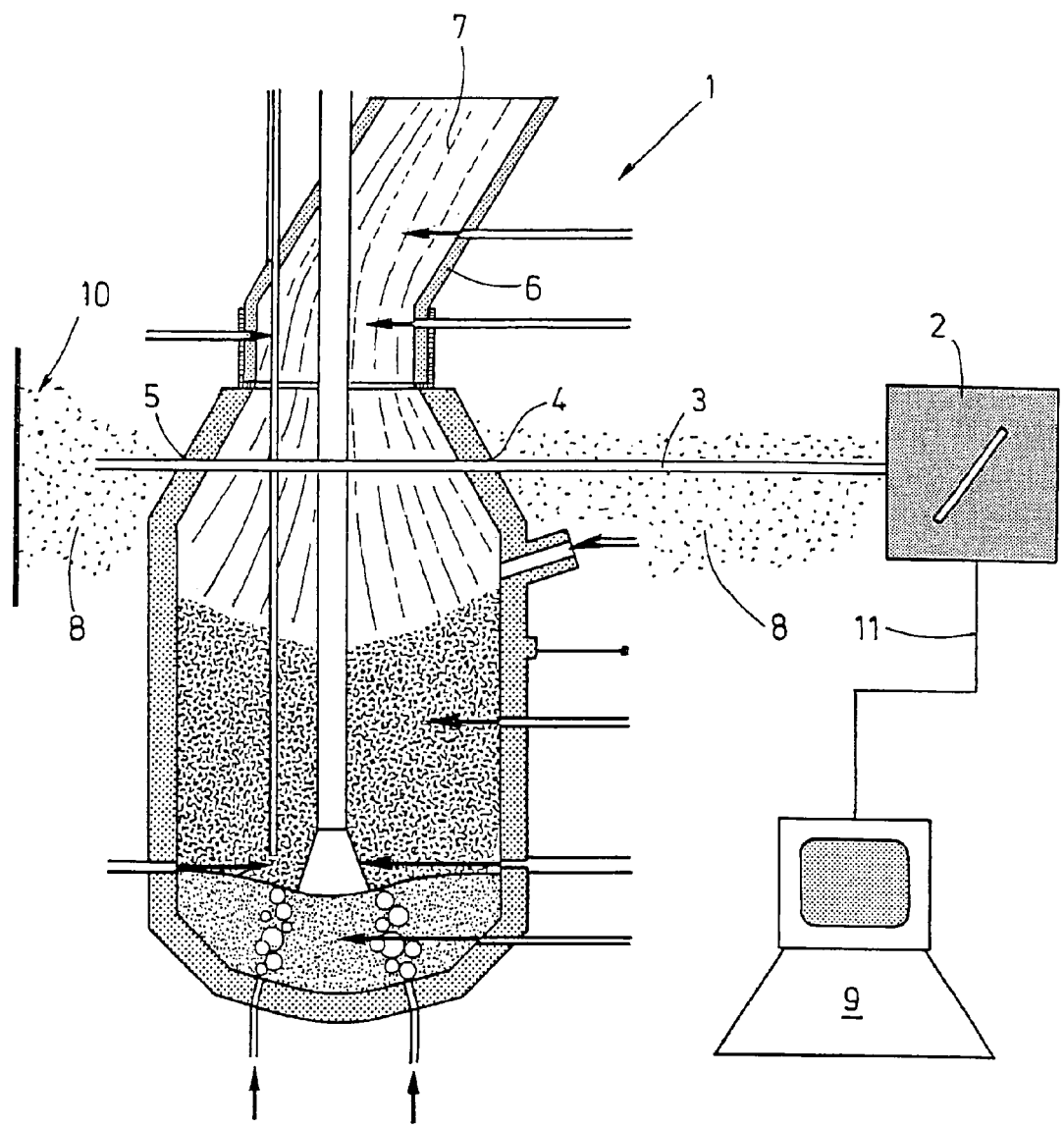

NON-CONTACT EXHAUST GAS MEASUREMENT BY MEANS OF FTIR SPECTROMETRY IN METALLURGICAL INSTALLATIONS

The invention relates to a method of non-contact exhaust gas measurement in metallurgical installations or plants in hot and dirty air, in particular, in a converter with a FTIR-spectrometer (FTIR-Fourier Transform Infra Red) which is mounted at a distance from a metallurgical installation and a measurement beam of which is directed in a suitable opening of an exhaust gas channel as a measurement point in an exhaust gas, wherein in accordance with a measurement beam length in the exhaust gas, an exhaust gas volumetric segment in form of a cylinder of the measurement beam length is metrologically detected, and thereby obtained measurement values are presented by the FTIR-spectrometer as spectra dependent on an exhaust gas composition and which enable, with inclusion of an exhaust gas temperature and using a previously established mathematical model that was obtained based on a temperature-dependent energy balance, calculation of the exhaust gas composition without a time delay.

During carrying out of metallurgical processes in plant components such as, e.g., a converter, knowledge of a time-dependent exhaust gas composition provides a significant aid in obtaining information about the process advancement and for ability to correspondingly control the same. A known possible analytical method consists, e.g., in taking of a limited volume from the exhaust gas flow and then analyzing this exhaust gas sample metrologically, as it is described, e.g., in German Patent 42 17 933 C2 for determining an end point for oxidizing process in oxygen converters.

The drawback of the analytical method based on sampling consists in a time delay with which the analysis results are obtained after a sample was taken, because beforehand the hot exhaust gas is cooled and must be eventually made ready for the analysis. A further drawback consists in the necessity to clean the sampling system (lances, tubular conduits) because the exhaust gas is dirty, which leads to interruptions that also lead to the time delay before the results of the analysis are received. Finally, exact analysis results are achieved only when the exhaust gas sample is taken from a flow having uniform cross-sectional profile, that is why this and also because of the small sample volume may not be absolutely representative.

In order to eliminate these drawbacks, a report of O. Jannasch, H.-W. Gudenau, K. Mavromanatis, D. Senk: "Determination of Post-Combustion in an Electrical Arc Furnace with FTIR-Exhaust Gas Analysis," Lecture $18^{th}$ Aachen Steel colloquium, September 25 and 26, Conference Reports, Mainz, Aachen, proposes a method with which a non-contact exhaust gas analysis can be carried out without a noticeable time delay.

For carrying out the non-contact exhaust gas analysis, a FTIR-spectrometer, the measurement beam (laser beam) of which is directed in a slot of the exhaust gas bend, is mounted on a platform sidewise of an electrical arc furnace at a distance therefrom. Based on the measurement results in form of temperature-dependent spectra and the exhaust gas components which were obtained with a conventional analyzer based on sampling for comparison purposes, there developed a mathematical model in form of an energy balance adapted to conditions of an electrical steel plant. The following combination of the developed model with actual values of a FTIR-spectrometry provides a rapid non-contact exhaust gas analyzing method that can be used for post-combustion in the electrical arc furnace that should lead to an efficient use of the energy which is contained in the exhaust gas.

Proceeding from the described state of the art, the object of the invention is to expand the method of non-contact exhaust gas analysis, which was developed for electrical arc furnaces, for other metallurgical installations that operate in a hotter and more dirty environment, in particular, for converters, to adapt it to such installations, and to provide a suitable apparatus for its carrying-out.

The set object is achieved with a method with characterized features of claim 1 that firstly, the mathematical model, on which the calculation of the exhaust gas composition is based, is adapted to a hot and dirty surrounding air that is also caught by the measurement beam, and to specific temperatures and exhaust gas compositions of a corresponding metallurgical installation, in particular, of a converter, and correspondingly is reworked anew, whereby reference spectra are produced by calibration, and in addition to spectroscopical determination of the exhaust gas composition, flow characteristics (laminar or turbulent components) of the exhaust gas are determined and used to support calculations when the model is established.

A device for carrying out the non-contact exhaust gas analysis method is characterized by features of claim 6. Other embodiments of the invention are given in sub-claims.

The measurement point for the FTIR-spectrometer at a suitable point o the exhaust gas channel is so selected that a linear measurement beam, which is emitted by the FTIR-spectrometer, can be guided through the first front measurement opening of the exhaust gas channel, then in a free passage through the exhaust gas and, finally, through a rearside second measurement opening of the exhaust gas channel to a rearside cold background located outside of the exhaust gas channel. The cold background, which is necessary for the spectroscopical exhaust gas analysis as a reference point, should be located as close as possible behind the exhaust gas channel. The necessary, for as precise as possible measurement, an exact alignment of the measurement beam of the FTIR-spectrometer through the measurement openings of the exhaust gas channel which form the measurement point, can be carried out, as desired, with a mirror system. Additionally, the undertaken determination of the flow characteristic of the exhaust gases, which is undertook in support of developing the model, according to the invention, is carried out with a CCD-camera that is installed at the measurement point of the FTIR-spectrometer or in an immediate vicinity of the measurement point.

Because both the FTIR-spectrometer and the CCD-camera are located in a hot vicinity of the to-be-measured metallurgical installation, it is absolutely necessary to appropriately protect both sensitive and also expensive apparatuses, in particular to cool them, e.g., with liquid nitrogen.

Because of the spatial distance of the FTIR-spectrometer and of the cold background from the exhaust gas channel, during conducting of the spectral measurement, not only internal content of the exhaust gas is sensed but in the same way the dirty surrounding air, which fills the space between the exhaust gas channel and the FTIR-spectrometer or the cold background, is sensed. At forming the mathematical model, these materials, which do not belong to the exhaust gas should be taken into account and eliminated to avoid a later false interpretation of the measurement results.

The cold background is necessary for calibration of the spectrometer. A cold background does not emit any infra-red radiation, so that the spectrometer constantly receives a reference for recording the spectra of the hot, to be measured exhaust gas.

The distance between the measurement point and spectrometer can amount, in an ideal case, to between 15 m and 30 m; with longer distances an amplifier is needed. With measurement sites, where no direct visual contact between the measurement point and the location point of the spectrometer is possible, a mirror system, eventually, in connection with an amplifier, must be used. Such measures lead to worsening of the signal quality. It is difficult to fix the upper limit of deviations, those should be determined experimentally and are strongly dependent on the exhaust gas quality and on the absorption of the signal by the dirty air between the measurement point and the location of the spectrometer.

The mathematical model is necessary because each gas molecule shows, dependent on the temperature, strong differences in spectra (number of waves and form). The intensity of the spectrum (maximum of emissivity) provides information of a portion of these molecules in the whole exhaust gas. The mathematical model provides exact correlations.

There are two working modes for the infrared spectroscopy: active and passive modes. Only in the active mode, a real measurement beam exists. Hier, gas measurement is encouraged, it is in this mode, the cold background absorbs all of the energy, without any reflection. An operational passive mode uses energy which is stored in the exhaust gas. The energy stimulates translational and rotational movement of the exhaust gas molecules, which is sensed by the spectrometer. A cold background shows no such activities, a so-called "zero activity" that can be used as a reference for the spectrometer.

The apparatus for carrying out a non-contact exhaust gas measurement in hot and dirty surrounding air is characterized in that a FTIR-converter, which is supported vibration-free on a platform adjacent to a metallurgical installation, is so positioned on the platform that a measurement beam can be directed through a suitable measurement point with openings in the exhaust gas channel through the exhaust gas and onto a rearside cold background, and a so-aligned mounted CCD-camera records flow characteristics of the exhaust gas simultaneously with or only with a small time delay relative to a spectroscopical determination of the exhaust gas composition.

Because for effecting the measurement, the FTIR-spectrometer is mounted in the vicinity of the exhaust gas channel and, thereby, is located in a hot and dirty surrounding air and is sensitive, e.g., to electromagnetic fields, which are generated by transformers, the FTIR-spectrometer is located, for protection from the dirt of the surrounding air in a sheet metal housing that is lined with mu-metal for protection from eventual electromagnetic fields. If necessary, the CCD-camera can also be located in this sheet metal housing.

For protection against the high temperature of the surrounding air, the FTIR-spectrometer or the detector and/or the sheet metal housing are connected with a cooling device that is supplied, e.g., with liquid nitrogen.

The FTIR-spectrometer and the CCD-chamber are connected with a measurement computer by corresponding conductors or by radio waves, and which is placed at a measuring station of the metallurgical installation, providing for evaluation of the measurement results at a clean location with a moderate temperature.

Further particularities, features, and advantages of the invention will be explained below in detail with reference to an embodiment shown in a schematic drawing figure.

The drawing figure shows a conventional converter and, therefore, explanation of the constructional detail would be dispensed with. The upper end of the converter 1 forms an exhaust gas channel 6 through which hot exhaust gases 7 are removed from the converter 1. At a spatial distance from the converter 1, at an increased, in comparison with the converter size, scale, there is shown a measurement device for a spectroscopic exhaust gas analysis and which consists of FTIR-spectrometer 2, a cold background 10, and a measuring computer 9 that is connected with the FTIR-spectrometer 2 by a connection conductor 11. The FTIR-spectrometer 2 is shown as a black box that should symbolize a sheathed sheet metal box, and is mounted on a platform (not shown) at such a height that the measurement beam 3 of the FTIR-spectrometer 2 is directed horizontally onto an exhaust gas-conducting portion of the converter 1.

Criteria for the installation location of the FTIR-spectrometer 2 are determined by the availability or the possibility to form suitable measurement openings 4 and 5 in the exhaust gas channel 6 that would permit entry of as small as possible amount of secondary air in the exhaust gas 7 through the measurement openings 4 and 5, and further of cold background 10 located behind the exhaust gas channel 6 at a height of the measurement beam 3.

In the shown embodiment, the measurement beam 3, which is emitted by the FTIR-spectrometer 2, enters the front measurement opening 4 in the upper portion of the converter 1 or in the lower portion of the exhaust gas channel 6, passes through the exhaust gas 7 in the horizontal direction, and exits finally, after leaving the exhaust gas channel 6, through the rear measurement opening 5, striking the cold background 10 spaced from the converter. In its path from the FTIR-spectrometer 2 to the cold background 10, the measurement beam 3 runs not only through the exhaust gas along a length that corresponds to the distance of both measurement openings 4 and 5 from each other, but also through the hot and dirty air 8 surrounding the converter 1. The difficulty here consists in that the composition and the temperature of the surrounding air can vary in an undefined manner and, therefore, can be different in front of and behind the converter 1. Therefore, in the to-be-established mathematical model, these values, independent from the exhaust gas composition to the most possible extent, should be taken into consideration by corresponding preliminary tests and calibration during establishing of reference spectra which are to be used in the mathematical model.

LIST OF REFERENCE NUMERALS

1 Converter
2 FTIR-Spectrometer
3 Measurement beam
4 Front measurement opening
5 Rear measurement opening
6 Exhaust gas channel
7 Exhaust gas
8 Surrounding air
9 Measurement computer
10 Cold background
11 Connection conductor

The invention claimed is:

1. A method of a non-contact exhaust gas measurement in metallurgical installations in hot and dirty air (8), in particular, in a converter (1) with a FTIR-spectrometer (2) which is mounted at a distance from a metallurgical installation and a measurement beam (3) of which is directed in a suitable opening (4) of an exhaust gas channel (6) as a measurement point in an exhaust gas (7), wherein in accordance with a measurement beam length in the exhaust gas (7), an exhaust gas volumetric segment in form of a cylinder of the measurement beam length is metrologically detected, and thereby obtained measurement values are presented by the FTIR-spectrometer (2) as spectra dependent on an exhaust gas composition and which enable, with inclusion of an exhaust gas temperature and using a previously established mathematical model that was obtained based on a temperature-dependent energy balance, calculation of the exhaust gas composition without a time delay, characterized in that a) firstly, the mathematical model, on which the calculation of the exhaust gas composition is based, is adapted to a hot and dirty surrounding air (8) that is also caught by the measurement beam (3), and to specific temperatures and exhaust gas compositions of a corresponding metallurgical installation, in particular, of a converter (1), and correspondingly is reworked anew, whereby reference spectra are produced by calibration, and b) in addition to spectroscopical determination of the exhaust gas composition, flow characteristics (laminar or turbulent components) of the exhaust gas are determined and used to support calculations when the model is established, c) the measurement point (4) for the FTIR-spectrometer (2) is so selected that a linear measurement beam (3), which is emitted by the FTIR-spectrometer (2), can be guided through the first front measurement opening (4) of the exhaust gas channel (6), then in a free passage through the exhaust gas (7) and, finally, through a rearside second measurement opening (5) of the exhaust gas channel (6) to a rearside cold background (10) outside of the exhaust gas channel (6).

2. A method according to claim 1,
characterized in that
at the measurement point (4) of the FTIR-spectrometer (2) or in an immediate vicinity of the measurement point (4), a mounted CCD-camera is used for determining the flow characteristics of the exhaust gas (7).

3. A method according to claim 1,
characterized in that
an exact alignment of the measurement beam (3) of the FTIR-spectrometer (2) through the measurement openings (4, 5) of the exhaust gas channel (6) of the measurement point is carried out with a mirror system.

4. A method according to claim 1,
characterized in that
the FTIR-spectrometer and, if needed, the CCD-camera are cooled.

5. An apparatus for carrying out a non-contact exhaust gas measurement in metallurgical installations in hot and dirty surrounding air (8), in particular in a converter (1) including an exhaust gas channel (6) having a first frontside opening (4) and a second rearside opening (5); and a rearside cold background (10) outside of the exhaust gas channel (6), the apparatus comprising:

a FTIR-spectrometer mounted at a distance from the metallurgical installation vibration-free on a platform and so positioned on the platform that a linear measurement beam (3), which is emitted by the FTIR-spectrometer (2), can be guided through the first frontside measurement opening (4) of the exhaust gas channel (6), then in a free passage through the exhaust gas (7) and, finally, through the rearside second measurement opening (5) of the exhaust gas channel (6) to the rearside cold background (10); and a mounted CCD-camera for recording flow characteristics (laminar or turbulent components) of the exhaust gas (7) simultaneously with or only with a small time delay relative to a spectroscopical determination of the exhaust gas composition, wherein in accordance with a measurement beam length in the exhaust gas (7), an exhaust gas volumetric segment in form of a cylinder of the measurement beam length is metrologically detected, and thereby obtained measurement values are presented by the FTIR-spectrometer (2) as spectra dependent on an exhaust gas composition and which enable, with inclusion of an exhaust gas temperature and using a previously established mathematical model that was obtained based on a temperature-dependent energy balance, calculation of the exhaust gas composition without a time delay, and adapted to a hot and dirty surrounding air (8) that is also caught by the measurement beam (3), and to specific temperatures and exhaust gas compositions of the corresponding metallurgical installation, in particular, of the converter (1), and correspondingly is reworked anew, whereby reference spectra are produced by calibration, and wherein the flow characteristics of the exhaust gas determined with the CCU-camera are used to support calculations when the model is established.

6. An apparatus according to claim 5,
characterized in that
the FTIR-spectrometer is enclosed in a street metal housing lined with mu-metal for protection against dirt and existing electro-magnetic fields.

7. An apparatus according to claim 5
characterized in that
the FTIR-spectrometer (2) (the detector) and/or the sheet metal housing and, if needed, the CCD-camera are connected with a cooling device which, e.g., is supplied with liquid nitrogen.

8. An apparatus according to claim 5,
characterized in that
the FTIR-spectrometer and the CCD-camera are connected with a measurement computer.

* * * * *